(12) United States Patent
Wu (10) Patent No.: US 7,223,792 B2
(45) Date of Patent: May 29, 2007

(54) **CYTOTOXIC ANNONACEOUS ACETOGENINS FROM *ANNONA MURICATA***

(75) Inventor: Yang-Chang Wu, No. 100, Shih-Chuan 1st Road, Kaohsiung (TW)

(73) Assignees: Yang-Chang Wu, Kachsiung (TW); Advpharma Inc., Hou-Bi Tainan (TW)

(*) Notice: Subject to any disclaimer, the term of this patent is extended or adjusted under 35 U.S.C. 154(b) by 874 days.

(21) Appl. No.: 10/005,324

(22) Filed: Dec. 7, 2001

(65) Prior Publication Data
US 2003/0144348 A1    Jul. 31, 2003

(51) Int. Cl.
*A61K 31/34* (2006.01)
*C07D 307/34* (2006.01)
*C07D 307/26* (2006.01)

(52) U.S. Cl. .................. 514/473; 549/320; 549/323

(58) Field of Classification Search ............... 549/320, 549/323; 514/473
See application file for complete search history.

(56) References Cited

U.S. PATENT DOCUMENTS 5,955,497 A * 9/1999 McLaughlin et al. ....... 514/473
6,242,483 B1 * 6/2001 McLaughline et al. ..... 514/473

OTHER PUBLICATIONS

Grever et al, Seminars in Oncology, vol. 19 No. 6 (Dec. 1992), The National Cance Institute: Cancer Drug Discovery and Development Program, pp. 622-628.*

Alali, F.Q. et al.; Annonaceous Acetogenins: Recent Progress; Invited Review; J. Nat. Prod., 1999, vol. 62, pp. 504-540.

Li, Chao Ming et al.; Three New Bioactive Annonaceous Acetogeninins from *Annona muricata*; Chinese Chemical Letters, 1994, vol. 5, No. 9, pp. 747-750.

Rieser, Matthew J. et al.; Muricatetrocins A and B and Gigantetrocin B: Three New Cytotoxic Monotetrahydrofuran-Ring Acetogenins from *Annona muricata*; Helvetica Chimica Acta, 1993, vol. 76, pp. 2433-2444.

Liaw, Chih-Chuang et al.; New Annonaceous Acetogenins from *Rollinia mucosa*; J. Nat. Prod., 1999, vol. 62, pp. 1613-1617.

Chang, Fang-Rong et al.; Bioactive acetogenins from the seeds of *Annona atemoya*; Phytochemistry, vol. 51, 1999, pp. 883-889.

Chen, Chung-Yi et al.; Aromin-A, an Annonaceous acetogenin from *Annona cherimola*; Phytochemistry, vol. 51, 1999, pp. 429-433.

Hoye, Thomas R. et al.; Stereostructural Studies on the 4-Hydroxylated Annonaceous Acetogenins: A Novel Use of Mosher Ester Data for Determining *Relative* Configuration [Between C(4) and C(36)]; Tetrahedron Letters, vol. 35, 1994, No. 46, pp. 8529-8532.

(Continued)

*Primary Examiner*—Cecilia J. Tsang
*Assistant Examiner*—Raymond Covington
(74) *Attorney, Agent, or Firm*—Fei-Fei Chao; Bingham McCutchen LLP (57) ABSTRACT

Acetogenins isolated from *Annona muricata* of the family Annonaceae are described. The substantially pure compounds of the invention exhibit to human tumor cell lines as well as selective cytotoxicity for various human tumor cell lines.

10 Claims, 6 Drawing Sheets

OTHER PUBLICATIONS

Chavez, Daniel et al.; Purprediolin and Purpurenin, Two New Cytotoxic Adjacent Bis-tetrahydrofuran Annonaceous Acetogenins from the Seeds of *Annona purpurea*; J. Nat. Prod., 1998, vol. 61, pp. 580-584.

Gawronski, J. et al.; A Note on the Determination of Absolute Configuration of Acetogenins by Circular Dichroism; Polish J. Chem., 1999, vol. 73, pp. 241-243.

Fujimoto, Yoshinori et al.; Annonaceous Acetogenins from the Seeds of *Annona squamosa*, Non-adjacent Bis-tetrahydrofuranic Acetogenins; Chem. Pharm. Bull. vol. 42(6), 1994, pp. 1175-1184.

Miyoshi, Hideto et al.; Essential structural factors of annonaceous acetogenins as potent inhibitors of mitochondrial complex I; Biochimica et Biophysica Acta, vol. 1365, 1998, pp. 443-452.

* cited by examiner

CYTOTOXIC ANNONACEOUS ACETOGENINS FROM *ANNONA MURICATA*

BACKGROUND OF THE INVENTION

1. Field of the Invention

This invention relates to the isolation, identification and use of natural products as anti-tumor agents. More particularly, the present invention relates to seven new annonaceous acetogenins from *Annona muricata*, muricin A, B, C, D, E, F, and G, and their use in treating patients having tumors, and even some with hepatoma cancer.

2. Description of Related Art

Many plants of the Annonaceae have been used in folk medicine and insecticides. Among the constituents of these materials, annonaceous acetogenins, known to have potent anticancer activities, are regarded as the major active principles. Annonaceous acetogenins, a rather new class of natural compounds only isolated from the Annonaceae, are usually $C_{35}$-$C_{37}$ fatty acid derivatives connecting a variable number of Tetrahydrofuran (THF) or Tetrahydropryan (THP) rings and lactone terminal moiety. So far, more than three hundred compounds, most of which were steric isomers, have been found and published, and their more biological activities, such as cytotoxic, antiparasitic, insecticide and immunosuppressive activities, have been further proved.

*Annona muricata* L. (Annonaceae) is a well-known tropical fruit tree named "sour sop" or "guanabana", which is mainly distributed in the Americas and in Southeast Asia. Currently, there have been more than forty annonaceous acetogenins isolated from the stems, leaves and seeds of this plant up. In the previous study of annonaceous acetogenins from *Annona muricata* by Li's el al., three annonaceous acetogenins, muricatin A, muricatin B, and muricatin C, were found from the extract of the stem bark. In those annonaceous acetogenins, four known compounds, muricatetrocin A, muricatetrocin B, corossolin, and corossolone, show special selective cytotoxicities against hepatoma cell lines, Hep $G_2$, and 2,2,15. These four compounds are discussed with seven newly discovered annonaceous acetogenins in the detailed description in cytotoxicities of curing hepatoma.

SUMMARY OF THE INVENTION

The main objective of the present invention is to disclose seven new annonaceous acetogenins, muricin A, B, C, D, E, F, and G, obtained from *Annona muricata*.

Another objective of the present invention is to disclose the curing features of eleven new and known annonaceous acetogenins in hepatoma cell lines.

Further benefits and advantages of the present invention will become apparent after a careful reading of the detailed description.

DETAILED DESCRIPTION OF THE INVENTION

This invention is directed to seven new Annonaceous acetogenins, muricin A (1), muricin B (2), muricin C (3), muricin D (4), muricin E (5), muricin F (6), and muricin G (7), isolated from *Annona muricata* in substantially pure form. As used herein, the term substantially pure form is defined as greater than 95% pure. In one embodiment, muricin A (1), B (2), C (3), D (4), E (5), F (6), and G (7), are isolated in greater than 99% pure form. Applicants have discovered that those seven compounds are cytotoxic to tumor cell lines, thus allowing their use for treating patients having a tumor.

In the present invention, these seven new annonaceous acetogenins, muricin A (1), B (2), C (3), D (4), E (5), F (6), and G (7), are disclosed in their chemical structures and chemical properties. These seven new annonaceous acetogenins are extracted from A. *muricata* seed as shown in the following experiment sections:

1. General Experiment Procedures:

Optical rotations were measured with a JASCO DIP-370 digital polarimeter. Melting points were determined using a Yanagimoto micro-melting point apparatus and were uncorrected. The IR spectra were measured on a Hitachi 260-30 spectrophotometer. $^1$H NMR (400 MHz) and $^{13}$C NMR (100 MHz) spectra in $CDCl_3$ were recorded with Varian NMR spectrometers, using TMS as the internal standard. LRFABMS and LREIMS were obtained with a JOEL JMS-SX/SX 102A mass spectrometer or a Quattro GC/MS spectrometer having a direct inlet system. HRFABMS were measured in a JEOL JMS-HX 110 mass spectrometer. CD was measured on a JASCO DIP 370 polarimeter. Si gel 60 (Macherey-Nagel, 230-400 mesh) was used for column chromatography; precoated Si gel plates (Macherey-Nagel, SIL G-25 $UV_{254}$, 0.25 mm) were used for analytical TLC, and precoated Si gel plates (Macherey-Nagel, SIL G/$UV_{254}$, 0.25 mm) were used for the preparative TLC. The spots were detected by spraying with Dragendorff's reagent or 50% $H_2SO_4$ and then heating on a hot plate. HPLX was performed on a JASCO PU-980 apparatus equipped with a UV-970 detector. Develosil ODS-5 (250×4.6 mm i.d.) and preparative ODS-5 (250×20 mm i.d.) columns were used for analytical and preparative purposes, respectively.

2. Plant Material:

The seeds of *Annona muricata* were collected from Chia-Yi City, Taiwan, Republic of China, in March 1997. A voucher specimen is deposited in the Graduate Institute of Natural Products, Kaohsiung, Taiwan, Republic of China.

3. Extraction and Isolation:

The seeds (1.0 kg) were extracted repeatedly with MeOH at room temperature. The combined MeOH extracts were evaporated and partitioned to yield $CHCl_3$ and aqueous extracts. The $CHCl_3$ layer afforded a waxy extract (ca. 200.6 g), positive to Kedde's reagent. The $CHCl_3$ layer was further separated into ten fractions by column chromatography on Si gel with gradient system of n-hexane-$CHCl_3$ (n-hexane-$CHCL_3$ 4:1 to pure $CHCl_3$) and $CHCl_3$-MeOH (pure $CHCl_3$ to $CHCl_3$-MeOH: 10:1). Longifolicin, corossolin, and corossolone were further purified from the eighth fraction by reversed-phase HPLC. Then, the remnant of the eighth fraction was combined with the ninth fraction and further separated into ten fractions by column chromatography with reversed-phase HPLC. Muricin A (1), muricin B (2), muricin C (3), and muricin F (6) were isolated and purified from the seventh fraction by a preparative reversed-phase HPLC (ODS-5 column) with 88:12 MeOH-water (flow rate of 2 mL/min; UV detector set at 225 nm). Muricin D (4), muricin E (5), and muricin G (7), as well as two known compounds, muricatetrocin A (8) and muricatetrocin B (9), were isolated and purified from the eighth fraction by a preparative reversed-phase HPLC with 86:14 MeOH-water (flow rate of 2 mL/min; UV detector set at 225 nm).

Annonaceous acetogenins compounds 1-9 were further studied in their molecular structure as following:

1. Muricin A (1) was obtained as a white waxy solid; $[\alpha]^{25}_D$+7.2° (c 0.25, CHCl$_3$); UV (MeOH) $\lambda_{max}$(log $\epsilon$) 210 (3.64) nm; IR(KBr) $v_{max}$3392 (OH), 2917, 2849, 1746 (OC=O), 1067 cm$^{-1}$; $^1$H NMR (CDCl$_3$, 400 MHz) and $^{13}$C NMR (CDCl$_3$, 100 MHz); FABMS m/z 597[M+H]$^+$; EIMS (30 eV) 381 (2), 363 (1), 351 (11), 333 (11), 281 (30), 263 (2), 239 (19), and 221 (5), see FIG. 1; HRFABMS m/z 597.4726 (calcd. For C$_{35}$H$_{65}$O$_7$, 597.4730).

The [M+Na]$^+$ peak in the FABMS at 619 m/z established the molecule weight as 596. The HRFABMS gave an [M+H]$^+$ peak at m/z 597.4726 (calcd. 597.4730), corresponding to the molecular formula, C$_{35}$H$_{65}$O$_7$. The UV spectral absorption at 210 mn and the IR spectral absorption at 1740 cm$^{-1}$ indicated the presence of an $\alpha,\beta$-unsaturated $\gamma$-lactone group, positive to Kedde's reagent. The successive EI-MS peaks at m/z 578, 560, and 542 implied the appearance of three hydroxyl groups at least. In the $^1$H-NMR spectrum, the signals at $\delta$ 7.18 (1H, H-33), 5.06 (1H, H-34), 3.81 (1H, H-4), 2.54 (1H, H-3a), 2.47 (1H, H-3b), and 1.41 (3H, H-35) verified the presence of an $\alpha,\beta$-unsaturated $\gamma$-lactone with a hydroxyl group at C-4 position (see Table 1).

TABLE 1

$^1$H- and $^{13}$C NMR Chemical Shifts of Compounds 1 and 2

| | Muricin A | | Muricin B | |
|---|---|---|---|---|
| | $\delta$ ($^1$H) | $\delta$ ($^{13}$C) | $\delta$ ($^1$H) | $\delta$ ($^{13}$C) |
| 1 | | 174.9 | | 174.6 |
| 2 | | 131.2 | | 131.9 |
| 3a | 2.54 (m) | 32.2 | 2.53 (m) | 32.4 |
| 3b | 2.47 (m) | | 2.49 (m) | |
| 4 | 3.81 (m) | 69.8 | 3.79 (m) | 69.8 |
| 5 | 1.2~1.5 | 37.1 | 1.2~1.5 | 37.2 |
| 6~13 | 1.2~1.5 | 25.3–29.8 | 1.2~1.5 | 25.5–30.4 |
| 14 | 1.2~1.5 | 35.3 | 1.2~1.5 | 35.4 |
| 15 | 3.81 (m) | 79.3 | 3.79 (m) | 79.3 |
| 16 | 1.97, 1.62 (m) | 25.3–29.8 | 1.98, 1.63 (m) | 25.5–30.4 |
| 17 | 1.97, 1.62 (m) | 25.3–29.8 | 1.98, 1.63 (m) | 25.5–30.4 |
| 18 | 3.81 (m) | 81.8 | 3.79 (m) | 81.8 |
| 19 | 3.41 (m) | 74.4 | 3.40 (m) | 74.5 |
| 20 | 1.5~1.6 | 33.1–33.3 | 1.5~1.6 | 33.3–33.7 |
| 21~24 | 1.2~1.5 | 25.3–29.8 | 1.2~1.5 | 25.5–30.4 |
| 25 | 1.2~1.5 | 33.1–33.3 | 1.2~1.5 | 33.3–33.7 |
| 26 | 3.41 (m) | 74.9$^a$ | 3.40 (m) | 74.7$^a$ |
| 27 | 3.41 (m) | 74.2$^a$ | 3.40 (m) | 74.3$^a$ |
| 28 | 1.2~1.5 | 33.1–33.3 | 1.2~1.5 | 33.3–33.7 |
| 29 | 1.2~1.5 | 25.3–29.8 | 1.2~1.5 | 25.5–30.4 |
| 30 | 1.2~1.5 | 31.8 | 1.2~1.5 | 31.9 |
| 31 | 1.2~1.5 | 22.5 | 1.2~1.5 | 22.7 |
| 32 | 0.86 (t, J=6.7) | 13.9 | 0.87 (t, J=6.7) | 14.1 |
| 33 | 7.18 (d, J=1.6) | 152.1 | 7.18 (d, J=1.2) | 151.9 |
| 34 | 5.06 (qd, J=6.8, 1.6) | 78.0 | 5.06 (qd, J=6.4, 1.2) | 78.0 |
| 35 | 1.41 (d, J=6.8) | 18.9 | 1.41 (d, J=6.8) | 19.1 |

$^a$Assignments may be interchangeable.

The signal at $\delta$ 3.81 (2H, H-15, 18), 3.41 (1H, H-19), as well as $^{13}$C-NMR peaks at $\delta$81.8 (C-18), 79.3 (C-15), 74.4 (C-19), indicated the presence of a mono-THF ring with one flanking hydroxyl in a threo-conformation. A close examination of the NMR spectrum showed the proton resonances for the two methylene groups of the mono-THF ring, which were observed at $\delta$ 1.97 (H-16a, 17a) and 1.62 (H-16b, 17b), were corresponding to the trans conformation. By making the (R) and (S)-Mosher ester derivatives and Hoey methodology, the absolute stereochemistries at C-4 and C-19 of the muricin A could be confirmed as (R) and (R) respectively (see Table 2).

TABLE 2

$^1$H NMR Data of the (S)- and (R)-Mosher Esters of 1 and 2

| | 1 | | | | 2 | | | |
|---|---|---|---|---|---|---|---|---|
| Protons | S-MTPA | R-MTPA | $\Delta \delta_{S-R}$ | Config | S-MTPA | R-MTPA | $\Delta \delta_{S-R}$ | config |
| H-3a | 2.67 | 2.68 | −0.01 | | 2.63 | 2.53 | +0.01 | |
| H-3b | 2.58 | 2.59 | −0.01 | | 2.57 | 2.40 | +0.17 | |
| H-33 | 6.96 | 6.96 | 0 | | 6.72 | 6.65 | +0.07 | |
| H-34 | 4.89 | 4.90 | −0.01 | 4 R | 5.09 | 5.05 | +0.04 | 4 S |
| H-15 | 3.87 | 3.88 | −0.01 | | 3.85 | 3.88 | −0.10 | |
| H-18 | 3.71 | 3.72 | −0.01 | 19 R | 3.80 | 3.82 | −0.02 | 19 R |

The two of these hydroxyl groups were suspected as the presence of a vicinal diol due to the proton signal at δ 3.41 (2H) and $^{13}$C NMR peaks at δ74.9 and 74.2. By making the acetonide derivative, the downfield shifts of two protons from δ3.41 to 3.60 for two of the three methylene protons on OH-bearing carbons and the chemical shift of six protons at δ1.36 (2×CH$_3$, s) in the $^1$H-NMR spectrum verified the presence of one vicinal diol (see Table 3). The conformation of this vicinal diol was assigned as threo based on a comparison of its NMR chemical shift with literature data.

trans/threo according to Fujimoto el al. (see Table 1). The normal-form tail of muricin B was corroborated by the absorptions in the IR at 1740 cm$^{-1}$ and UV $\lambda_{max}$ at 210 nm. The vicinal diol was confirmed by making its acetonide derivative and determined its conformation as threo based in the comparison of the $^{13}$C NMR and $^1$H-NMR data with muricin A.

Figure 1:
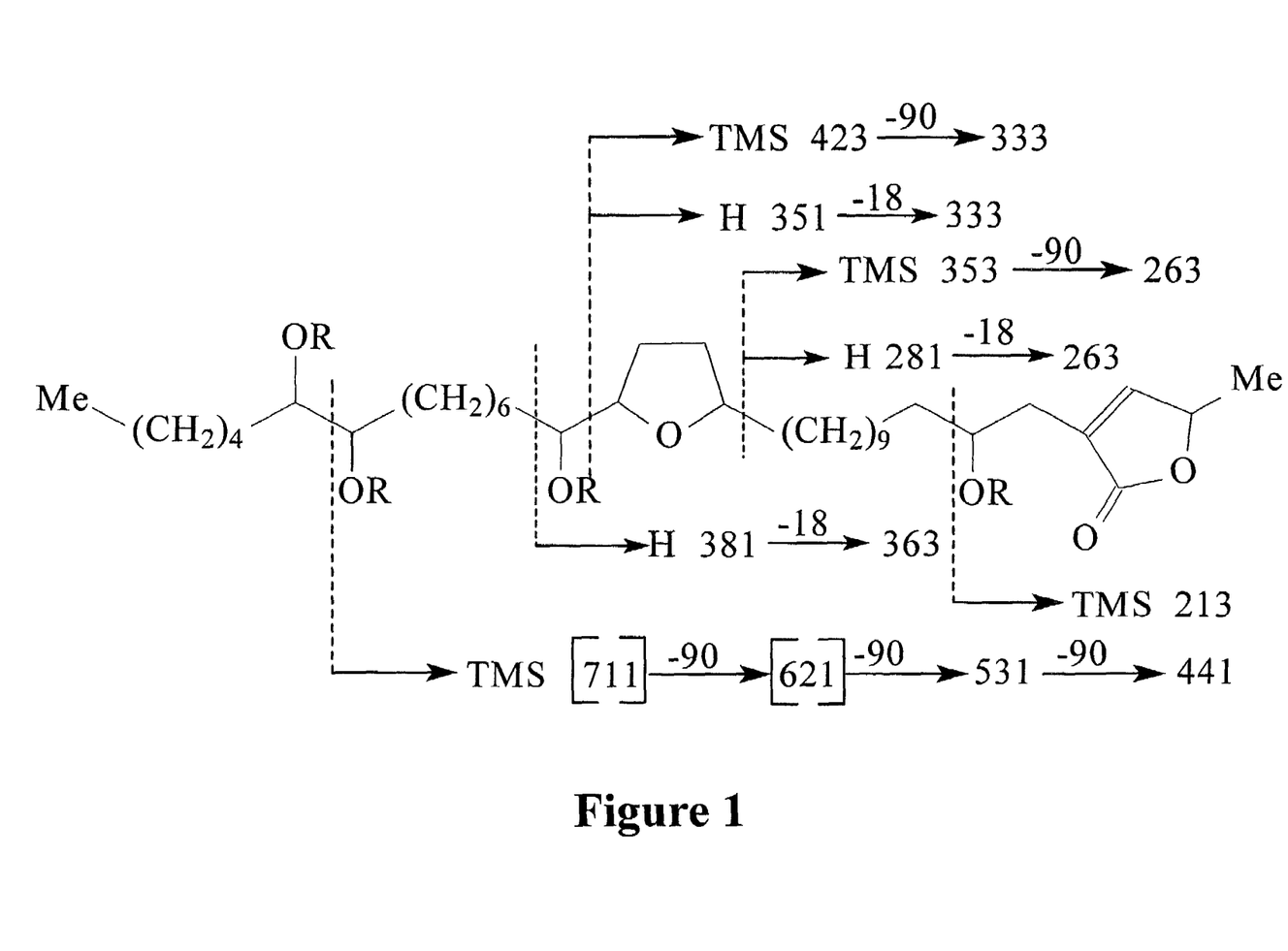
FIG. 1: The EI-MS Fragmentation of Muricin A (1) and Muricin B (2).

The EI-MS data of muricin B similar to one of muricin A determined the placement of the THF ring and the diol at C-15/C-18 and C-26/C-27, respectively (see FIG. 1). The

TABLE 3

$^1$H NMR Signals for the Protons of the Threo and Erythro Diols,$^{13}$ 1 and Acetonide 1b

|  | Methine protons | | Acetonyl methyls | |
| --- | --- | --- | --- | --- |
|  | threo | erythro | Threo | erythro |
| Diol | 3.45 (2H) | 3.62, 3.58 | | |
| Acetonide | 3.58 (2H) | 4.02, 4.00 | 1.37 (6H) | 1.43, 1.33 |
| 1 | | 3.41 (2H) | | |
| 1b | | 3.60 (2H) | 1.36 (6H) | |

The placement of the THF ring and the diol were established by close examination of EI-MS fragmentation of muricin A (see FIG. 1). The THF ring was placed between C-15 and C-18 based on the EI-MS fragmentation at m/z 351 and 281, and the vicinal diol was located at C-26/C-27 based on the EI-MS fragments at m/z ([711]→[621]→531 →441) of the TMS derivative.

Finally, the absolute configuration at C-34 of muricin A was determined by the CD method. According to a positive π–π*Cotton effect (Δε>0), it clearly indicated that the stereochemistry at C-34 on the γ-lactone fragment should be (S)-configuration.

2. Muricin B (2) was obtained as a white waxy solid; $[\alpha]^{25}_D$+0.2°(c 0.11, CHCl$_3$); UV (MeOH) $\gamma_{max}$(log ε) 210 (3.65) nm ; IR (KBr) $v_{max}$3419 (OH), 2918, 2849, 1738 (OC=O), 1067 cm$^{-1}$; $^1$H NMR (CDCl$_3$, 400 MHz) and $^{13}$C NMR (CDCl$_3$, 100 MHz) data; FABMS m/z 597[M+H]$^+$; EIMS (30 eV) 381 (2), 363 (1), 351 (10), 333 (11), 281 (30), 263 (2), 239 (19), 221 (5), see FIG. 1; HRFABMS m/z 597.4731 (calcd. for C$_{35}$H$_{65}$O$_7$, 597.4730).

Muricin B was separated and afforded following muricin A by reversed-phase HPLC with a solvent system MeOH/ H$_2$O (88/12), and muricin A and muricin B showed the completely different retention time at 13.7 min and 14.2 min, respectively (Develosil ODS-5 column, 250×4.6 mm i.d., flow rate of 1 mL/min). The HRFAB-MS gave an [M+H]$^+$ peak at m/z 597.4731 (calcd. 597.4730), corresponding to the molecular formula, C$_{35}$H$_{65}$O$_7$. Interestingly, from comparisons with the NMR spectral and MS data of muricin A, it was clearly indicated that muricin B had high similarity to muricin A. Like muricin A, the $^1$H and $^{13}$C-NMR signals indicated the presence of an α,β-unsaturated γ-lactone with a hydroxyl group at C-4 position and a mono THF ring with one flanking hydroxyl group in a relative conformation of positive π–π*Cotton effect (Δε>0) of muricin B in CD spectrum indicated the stereochemistry at C-34 on the γ-lactone fragment be (S)-configuration.

3. Muricin C (3) was obtained as a white waxy solid; $[\alpha]^{25}_D$+86.0° (c 0.15, CHCl$_3$); UV (MeOH) $\lambda_{max}$(log ε) 208 (3.73) nm; IR (KBr) $v_{max}$3440 (OH), 2930, 2833, 1745 (OC=O), 1027 cm$^{-1}$; $^1$H NMR (CDCl$_3$, 400 MHz) and $^{13}$C NMR (CDCl$_3$, 100 MHz) data; FABMS m/z 597 [M+H]$^+$; EIMS (30 eV) 449 (1), 431 (1), 409 (1), 391 (1), 379 (6), 361 (9), 309 (16), 291 (3), 267 (10), 239 (5), see FIG. 2; HRFABMS m/z 597.4732 (calcd. for C$_{35}$H$_{65}$O$_7$, 597.4730).

The HRFAB-MS gave an [M+H]$^+$ peak at m/z 597.4726 (calcd. 597.4730), corresponding to the molecular formula, C$_{35}$H$_{65}$O$_7$. The successive FAB-MS fragment at m/z 579, 561, 543, 525 suggested the presence of four hydroxyl groups. The UV absorption at 208 nm and the IR absorption at 1740 cm$^{-1}$ indicated the presence of an α,β-unsaturated γ-lactone with a hydroxyl group at C-4, a mono-THF ring with one flanking hydroxyl group, and a vicinal diol.

The signals of $^1$H-NMR spectrum at δ7.18 (1H, H-33), 5.0 6(1H, H-34), 3.86 (1H, H-4), 2.52 (1H, H-3a), 2.40 (1H, H-3b), 1.42 (3H, H-35), together with $^{13}$C-NMR peaks at δ174.6 (C-1), 151.8 (C-33), 131.2 (C-2) 78.0 (C-34), 70.0 (C-4), and 19.1 (C-35), were matched well the published data of an α,β-unsaturated γ-lactone with a hydroxyl group at C-4. The proton signals at δ3.86 (2H, H-17, 20), 3.43 (1H, H-21), 1.97 (2H, H-18a, 19a), 1.65 (2H, 18b, 19b), as well as $^{13}$C-NMR peaks at δ81.7 (C-20), 79.3 (C-17), and 74.4 (C-21), indicated the presence of a mono-THF ring with one flanking hydroxyl in relative of trans/threo or threoltrans conformation. Like muricin A, two of the four hydroxyl groups were determined as a diol due to the proton signal at δ3.43(2H) and $^{13}$C-NMR peaks at δ74.6-74.3 (see Table 4).

Figure 2:
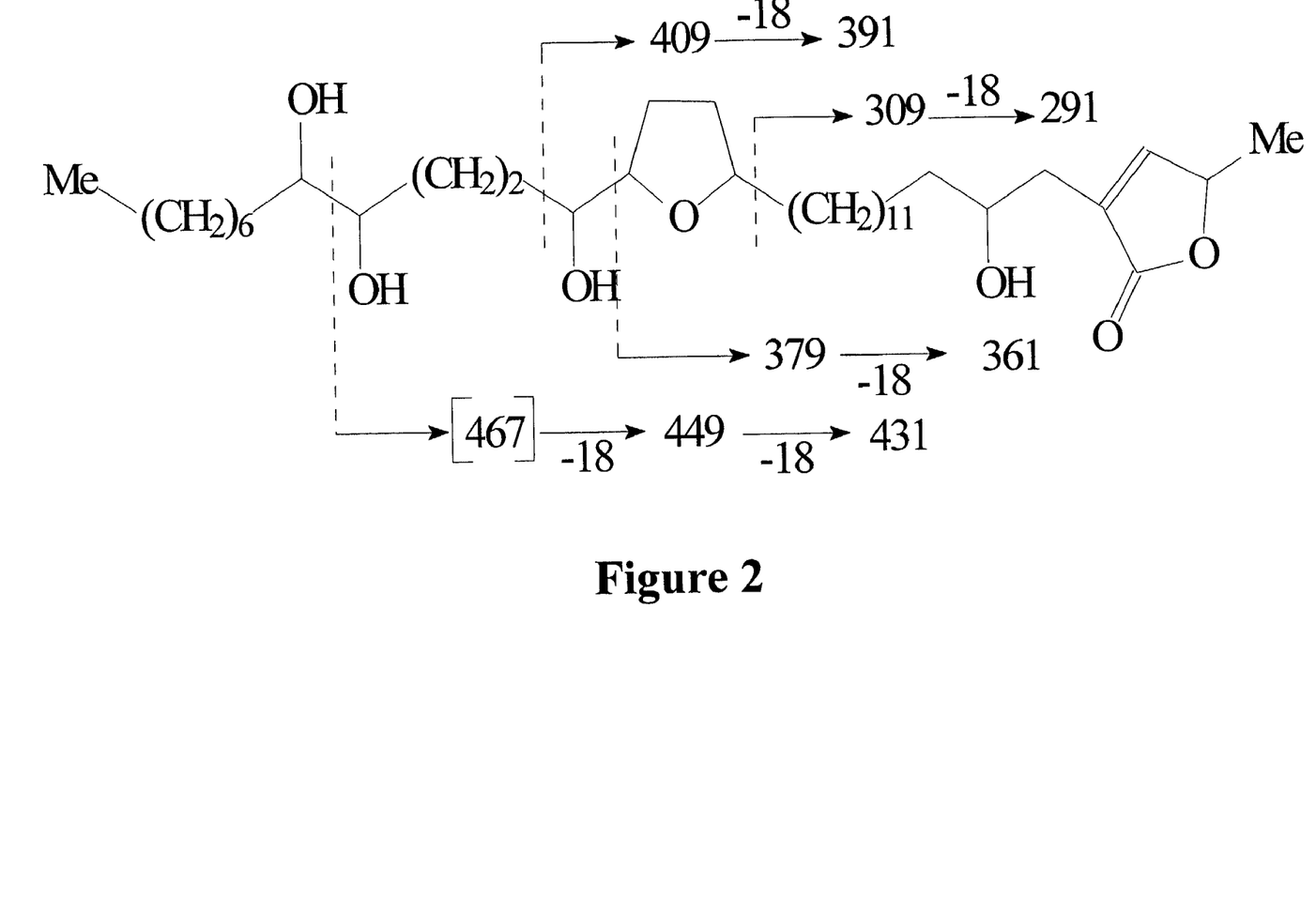
FIG. 2: The EI-MS Fragmentation of Muricin C (3)

The placements of the THF ring and hydroxyl groups were established by close examination of EI-MS fragmentation of muricin C (see FIG. 2). The THF ring was located between C-17/C-20 based on the EI-MS peaks at m/z 379 and 309, and the vicinal diol was placed between C-24/C-25 according to the EI-MS peaks at m/z ([467]→449→431).

Finally, the absolute configuration at C-34 of muricin C was determined by the CD method. The positive π-π*Cotton effect (Δε>0) clearly indicated the stereochemistry at the C-34 on the γ-lactone fragment was (S)-configuration. Additionally, muricin C is also the first example of annonaceous acetogenins that the THF ring began with an odd position C-17.

4. Muricin D (4) was obtained as white waxy solid; $[\alpha]^{25}_D$+77.6° (c 0.34, CHCl$_3$); UV (MeOH) $\lambda_{max}$(log ε) 208 (3.69) nm; IR (KBr) $v_{max}$3432 (OH), 2925, 2854, 1745 (OC=O), 1462, 1319, 1082 cm$^{-1}$; $^1$H NMR (CDCl$_3$, 400 MHz) and $^{13}$C NMR (CDCl$_3$, 100 MHz) data; FABMS m/z 569 [M+H]$^+$; EIMS (30 eV) 439 (1), 421 (1), 403 (1), 381 (2), 363 (1), 351 (30), 333 (21), 281 (64), 263 (4), 239 (40), 221 (7), see FIG. 3; HRFABMS m/z 569.4416 (calcd. for C$_{33}$H$_{60}$O$_7$, 569.4417).

The HRFAB-MS gave an [M+H]$^+$ peak at m/z 569.4416 (calcd. 569.4417), corresponding to the molecular formula C$_{33}$H$_{61}$O$_7$. The successive FAB-MS fragment at m/z 551, 533, 515, 497 suggested the presence of four hydroxyl groups. The IR absorption at 1740 cm$^{-1}$ and the UV absorption at 208 nm indicated the presence of a γ-lactone group. Comparisons with the $^1$H- and $^{13}$C-NMR spectral data of muricin A and muricin C suggested that muricin D also have the same moieties, an α,β-unsaturated γ-lactone with a hydroxyl group at C-4, a mono-THF ring diol with a conformation of threo according to the method of Fujimoto el al. (see Table 4).

Figure 3:
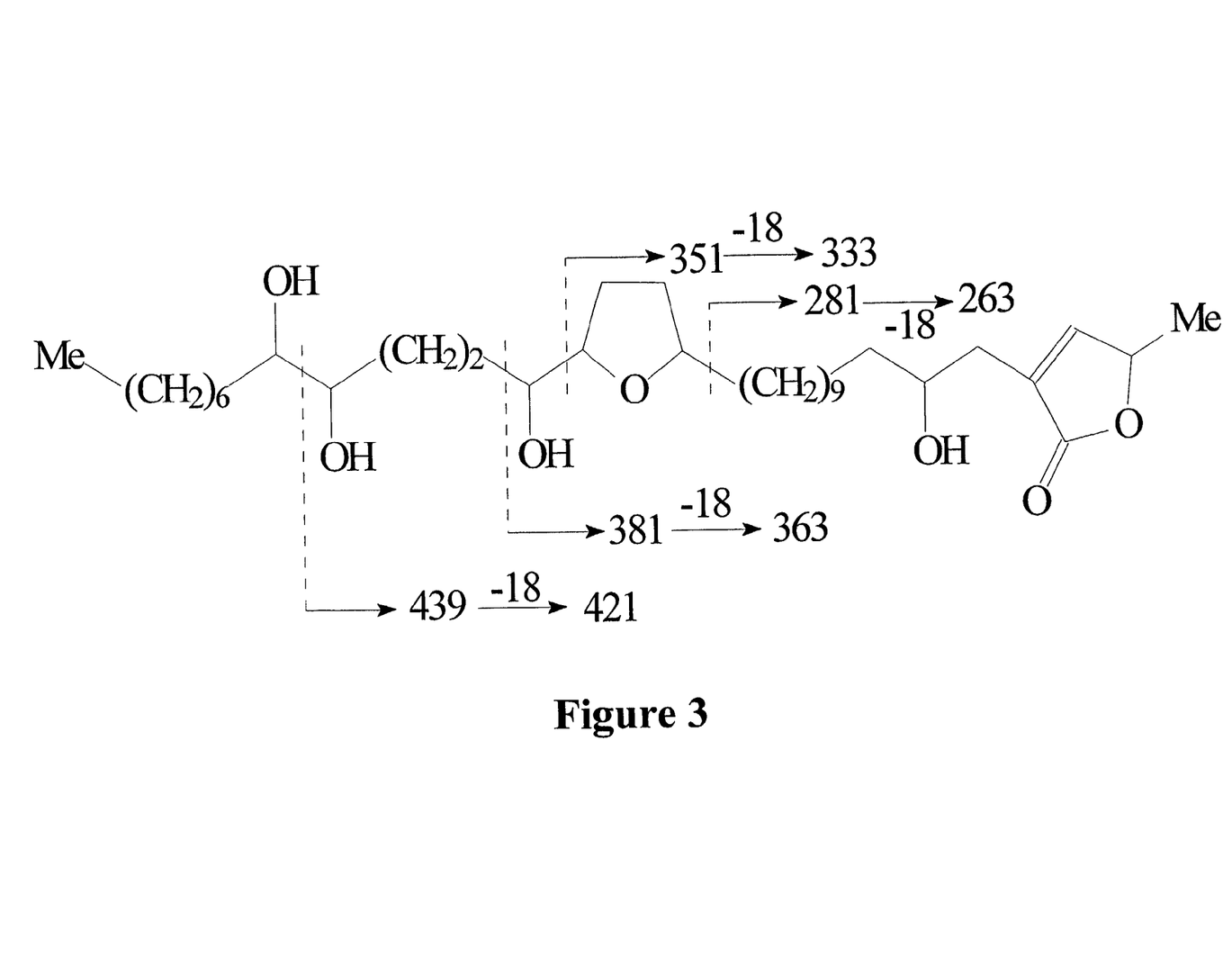
FIG. 3: The EI-MS Fragmentation of Muricin D (4)

The structure of the molecule was established by close examination of EI-MS fragmentation of muricin D (see FIG. 3). The fragments at m/z 351 and 281 indicated that the THF ring be located between C-15/C-18, and the fragments at m/z (439 →421) indicated the diol be located between C-22/C-23.

5. Muricin E (5) was obtained as a white waxy solid; $[\alpha]^{25}_D$+91.4° (c 0.23, CHCl$_3$); UV (MeOH) $\lambda_{max}$(log ε) 208 (3.62) nm ; IR (KBr) $v_{max}$3334 (OH), 2916, 2847, 1733 (OC=O), 1082 cm$^{-1}$; $^1$H NMR (CDCl$_3$, 400 MHz) and 13C NMR (CDCl$_3$, 100 MHz) data; FABMS m/z 569[M+H]$^+$; EIMS (30 eV) 421 (1), 403 (1), 351 (7), 333 (10), 309 (4), 291 (2), 263 (4), 239 (24) see FIG. 4; HRFABMS m/z 569.4417 (calcd. for C$_{33}$H$_{60}$O$_7$, 569.4417).

The HRFAB-MS gave an [M+H]$^+$ peak at m/z 569.4417 (calcd. 569.4417), corresponding to the molecular formula C$_{33}$H$_{61}$O$_7$. The successive FAB-MS fragments at m/z 551, 533, 515, and 497, suggested the presence of four hydroxyl groups. The IR absorption at 1740 cm$^{-1}$ and the UV absorption at 208 nm indicate the presence of a γ-lactone group. Comparisons with the NMR spectral data of muricin A and muricin C suggested that muricin E possesses the same moieties, an α,β-unsaturated γ-lactone with a hydroxyl group at C-4, a mono-THF ring with one flanking hydroxyl group in a conformation of threo/trans, and a vicinal diol with a conformation of threo according to the method of Fujimoto et al (see Table 4).

Figure 4:
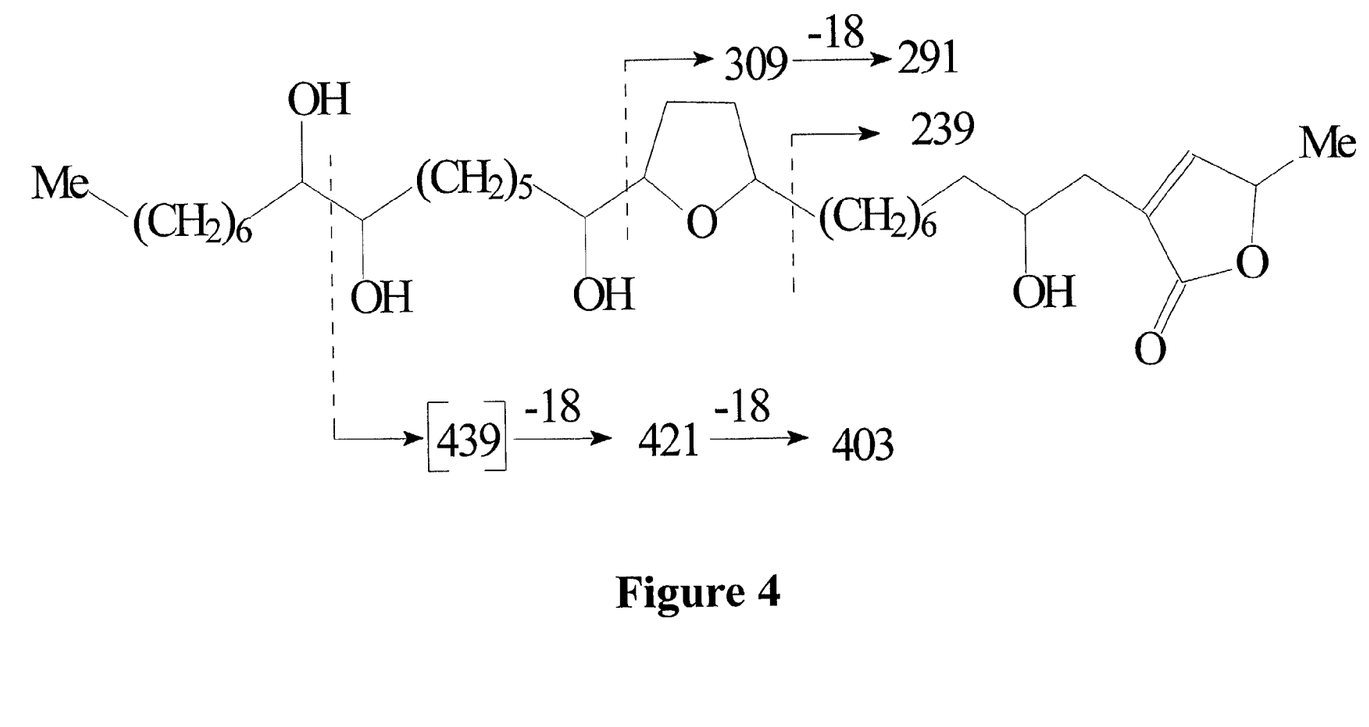
FIG. 4: The EI-MS Fragmentation of Muricin E (5)

The structure of the molecule was established by close examination of EI-MS fragmentation of muricin E (see FIG. 4). The fragment at m/z 309 and 239 demonstrated that the THF ring should be located between C-12/C-15, and the EI-MS fragments at m/z ([439 ]→421 →403) indicated the diol should be located between C-22/C-23.

6. Muricin F (6) was obtained as a white waxy solid; $[\alpha]^{25}_D$ +48.2° (c 0.48, CHCl$_3$); UV (MeOH) $\lambda_{max}$(log ε) 208 (3.89) nm ; IR (KBr) $v_{max}$3407 (OH), 2925, 2854, 1743 (OC=O), 1078 cm$^{-1}$; $^1$H NMR (CDCl$_3$, 400 MHz) and $^{13}$C NMR (CDCl$_3$, 100 MHz) data; FABMS m/z 595 [M+H]$^+$; EIMS (30 eV) 507 (1), 477 (1), 459 (1), 423 (1), 405 (1), 379 (2), 361 (2), 309 (7), 281 (15), 263 (3), 239 (12), 109 (13), see FIG. 5; HRFABMS m/z 595.4573 (calcd. for C$_{35}$H$_{62}$O$_7$, 595.4574).

The HRFAB-MS gave an [M+H]$^+$ peak at m/z 595.4573 (calcd. 595.4574), corresponding to the molecular formula C$_{33}$H$_{61}$O$_7$. The UV absorption at 208 nm and the IR absorption at 1743 cm$^{+1}$ indicated the presence of an α,β-unsaturated γ-lactone group. Comparisons with the NMR spectral data of muricin A and muricin F suggested that muricin F have the same moieties, an α,β-unsaturated γ-lactone with a hydroxyl group in a conformation of threo/trans, and a vicinal diol with a conformation of threo according to the methods of Fujimoto el al (see Table 5). Moreover, the proton signal at δ 5.39 (2H), together with $^{13}$C-NMR peaks at δ 130.1 and 129.5, showed the presence of a double bond.

TABLE 5

$^1$H- and $^{13}$C NMR Chemical Shifts of Compounds 6 and 7

| | Muricin F | | Muricin G | |
|---|---|---|---|---|
| | δ ($^1$H) | δ ($^{13}$C) | δ ($^1$H) | δ ($^{13}$C) |
| 1 | | 174.6 | | 174.6 |
| 2 | | 131.1 | | 131.1 |
| 3a | 2.52 (m) | 32.4 | 2.50 (m) | 33.3~33.4 |
| 3b | 2.40 (m) | | 2.41 (m) | |
| 4 | 3.80 (m) | 69.9 | 3.82 (m) | 69.9 |
| 5 | 1.2~1.5 | 37.4 | 1.2~1.5 | 37.3 |
| 6–8 | 1.2~1.5 | 25.5–29.9 | 1.2~1.5 | 25.5–29.9 |
| 9 | 1.2~1.5 | 25.5–29.9 | 1.2~1.5 | 33.3~33.4 |
| 10 | 1.2~1.5 | 25.5–29.9 | 3.58 | 71.7 |
| 11 | 1.2~1.5 | 25.5–29.9 | 1.2~1.5 | 33.3~33.4 |
| 12–13 | 1.2~1.5 | 25.5–29.9 | 1.2~1.5 | 25.5–29.9 |
| 14 | 1.2~1.5 | 25.5–29.9 | 1.2~1.5 | 37.2 |
| 15 | 1.2~1.5 | 25.5–29.9 | 3.43 (m) | 74.0 |
| 16 | 1.2~1.5 | 33.1–35.4 | 3.89 (m) | 82.6$^a$ |
| 17 | 3.86 (m) | 79.3 | 1.99, 1.65 (m) | 25.5–29.9 |
| 18 | 1.97, 1.65 (m) | 25.5–29.9 | 1.99, 1.65 (m) | 25.5–29.9 |
| 19 | 1.97, 1.65 (m) | 25.5–29.9 | 3.89 (m) | 82.6$^a$ |
| 20 | 3.86 (m) | 81.7 | 3.43 (m) | 73.5 |
| 21 | 3.43 (m) | 74.4$^a$ | 1.2~1.5 | 33.3~33.4 |
| 22 | 1.5~1.6 | 33.1–35.4 | 2.17 (m) | 25.5–29.9 |
| 23 | 2.01 | 25.5–29.9 | 5.36 (m) | 130.8 |
| 24 | 5.39 (m) | 130.1 | 5.36 (m) | 128.9 |
| 25 | 5.39 (m) | 129.5 | 2.17 (m) | 25.5–29.9 |
| 26 | 2.01 | 33.1–35.4 | 1.2~1.5 | 25.5–29.9 |
| 27 | 3.42 (m) | 74.6$^a$ | 1.2~1.5 | 25.5–29.9 |
| 28 | 3.42 (m) | 74.3$^a$ | 1.2~1.5 | 25.5–29.9 |
| 29 | 1.2~1.5 | 33.1–35.4 | 1.2~1.5 | 25.5–29.9 |
| 30 | 1.2~1.5 | 31.4 | 1.2~1.5 | 31.9 |
| 31 | 1.2~1.5 | 22.6 | 1.2~1.5 | 22.7 |
| 32 | 0.87 (t, J=6.7) | 14.0 | 0.87 (t, J=6.8) | 14.1 |

TABLE 5-continued

<sup></sup>¹H- and ¹³C NMR Chemical Shifts of Compounds 6 and 7

| | Muricin F | | Muricin G | |
|---|---|---|---|---|
| | δ (¹H) | δ (¹³C) | δ (¹H) | δ (¹³C) |
| 33 | 7.18 (d, J=1.2) | 151.9 | 7.18 (d, J=1.2) | 151.9 |
| 34 | 5.06 (qd, J=6.8, 1.2) | 78.0 | 5.05 (qd, J=6.8, 1.2) | 78.0 |
| 35 | 1.42 (d, J=6.8) | 19.1 | 1.41 (d, J=6.8) | 19.1 |

<sup>a</sup>Assignments may be interchangeable.

Figure 5:
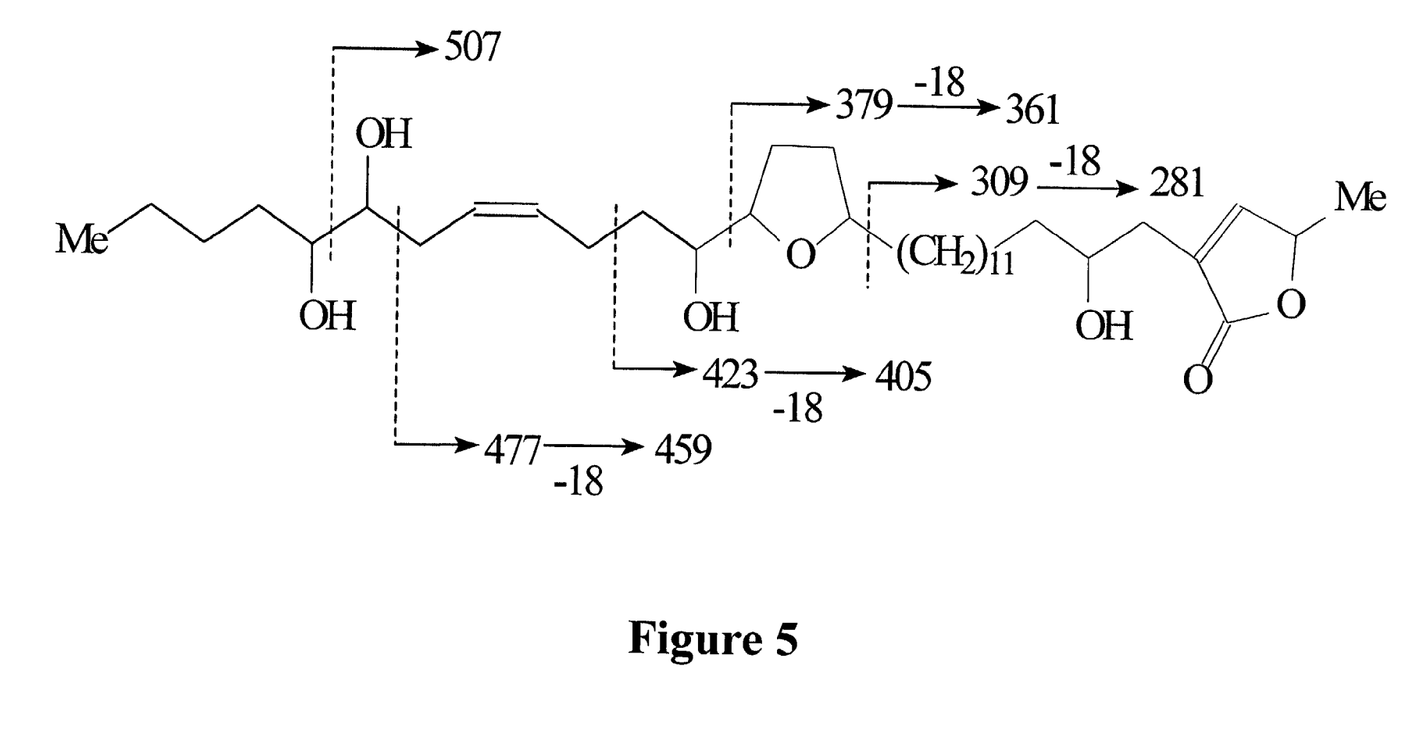
FIG. 5: The EI-MS Fragmentation of Muricin F (6)

The structure of the molecule was established by close examination of EI-MS fragmentation of muricin F (see FIG. 5). The EI-MS peaks of muricin F at m/z 379 and 309 demonstrated that the THF ring should be located between C-17/C-20. Furthermore, the position of the double bond was determined at C-24/C-25 based on the EI-MS peak at m/z 477 and 423. Finally, the EI-MS peak at m/z 507 indicated that the diol should be located between C-27/C-28.

7. Muricin G (7) was obtained as a white waxy solid; $[\alpha]^{25}_D$+47.0° (c 0.63, CHCl$_3$); UV (MeOH) $\lambda_{max}$(log ε) 210 (3.52) nm; IR (KBr) $\nu_{max}$3386(OH), 2931, 2859, 1748 (OC=O), 1081 cm$^{-1}$; ¹H NMR (CDCl$_3$, 400 MHz) and ¹³C NMR (CDCl$_3$, 100 MHz) data; FABMS m/z 595 [M+H]$^+$; EIMS (30 eV) 495 (1), 423 (1), 397 (1), 379 (2), 361 (6), 309 (44), 291 (15), 273 (7), 241 (13) see FIG. 6; HRFABMS m/z 595.4574 (calcd. for C$_{35}$H$_{62}$O$_7$, 595.4574).

The HRFABMS gave an [M+H]$^+$ peak at m/z 595.4574 (calcd. 595.4574), corresponding to the molecular formula, C$_{35}$H$_{63O7}$. The UV absorption at 210 nm and IR absorption at 1748 cm$^{-1}$ indicated the presence of an α,β-unsaturated γ-lactone group. In comparison with the NMR spectral data of muricin A and the published data of asiminenin B, Woo et al, Hetercycles, 41, 1731-1742 (1995), it was clearly suggested that muricin G has a high similarity to asiminenin B (see Table 5).

The proton signals at δ7.18 (1H, H-33), 5.05 (1H, H-34), 3.89 (1H, H-4), 2.50 (1H, H-3a), 2.41 (1H, H-3b), 1.41 (3H, H-35) together with ¹³C-NMR peaks at δ174.6 (C-1), 151.9 (C-33), 131.1 (C-2), 78.0 (C-34), 69.9 (C-4), 19.1 (C-35), were matched well with the published data of an α,β-unsaturated γ-lactone with a hydroxyl group at C-4 position. The proton signals at δ3.89 (2H, H-16, 19), 3.43 (2H, H-15, 20), 1.99 (2H, H-16a, 17a), 1.65 (2H, H-16b, 17b), as well as ¹³C-NMR peaks at δ82.6 (C-18), 74.0 (C-15) and 73.5 (C-19), indicated the presence of a mono-THF ring with two flanking hydroxyl groups in the conformation of threo/trans/threo according to the method of Fujimoto et al.

Figure 6:
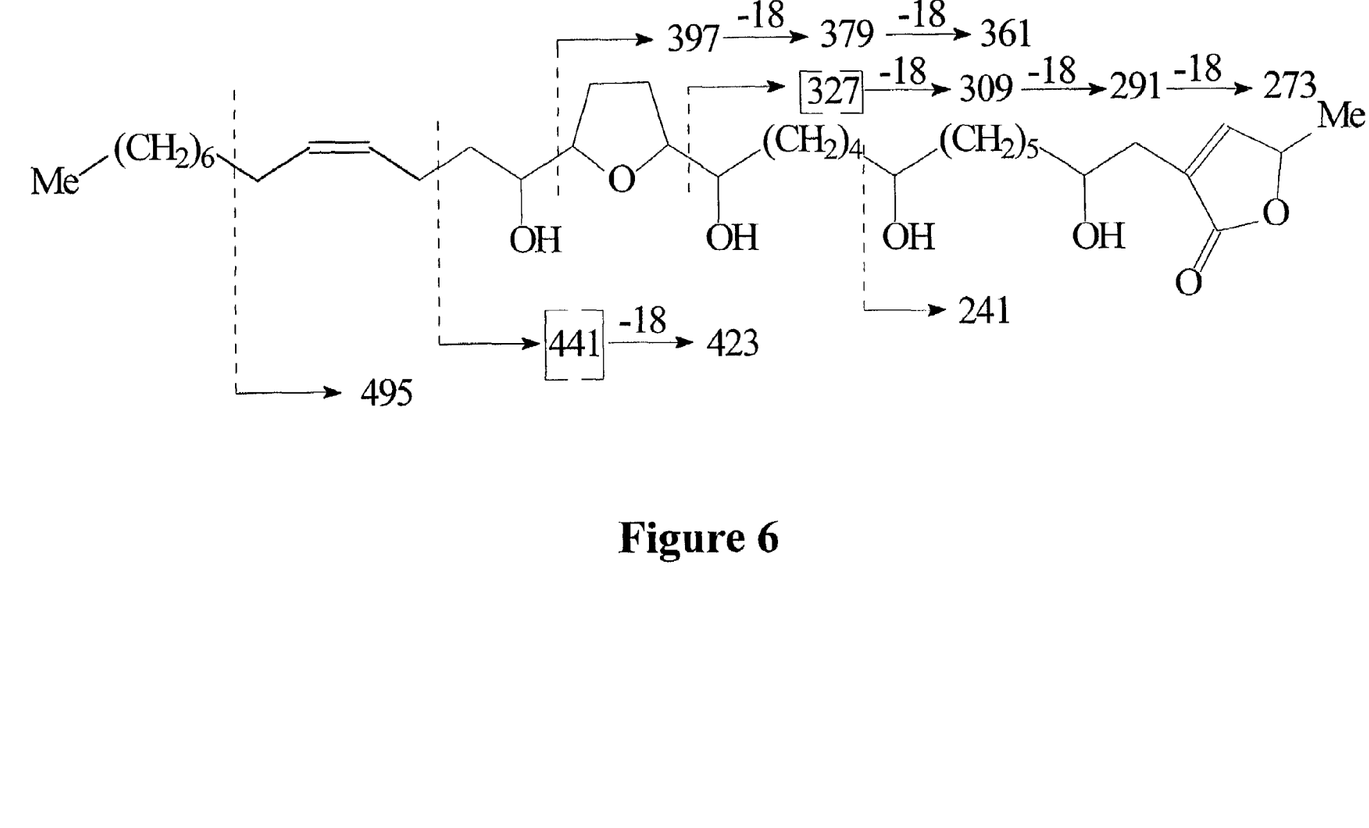
FIG. 6: The EI-MS Fragmentation of Muricin G (7)

The structure of the molecule was established by close examination of EI-MS fragment of muricin G (see FIG. 6). The EI-MS fragment at m/z 241 (cleavage between C-10/C-11) and its daughter peak at m/z 223 (cleavage between C-10/C-11—H$_2$O) suggested that the final hydroxyl group should be located at C-10. The EI-MS peaks at m/z 397 and 309 demonstrated the location of the THF ring should be between C-16/C-19. Finally, the peak at m/z 495 suggested that the double bond should be located at C-23/C-24.

All the CD spectra of compounds 4-7 were shown the positive π–π*Cotton effect (Δε>0), which indicated the stereochemistry at the C-34 on the γ-lactone fragment should be (S)-configuration as the same as muricin A, muricin B and muricin C.

8. A mixture of muricatetrocin A (8) and muricatetrocin B (9) was obtained as a colorless oil; $[\alpha]^{25}_D$ +22.2° (c 0.25, CHCl$_3$); UV (MeOH) $\lambda_{max}$(log ε) 210 (3.94) nm; UV, MS, ¹H- and ¹³C-NMR data were identical with published values (see reference 5).

9. Longifolicin (10) was obtained as a colorless oil; $[\alpha]^{25}_D$+8.3° (c 0.12, CHCl$_3$); UV (MeOH) $\lambda_{max}$(log ε) 208 (3.98) nm; UV, MS, ¹H- and ¹³C-NMR were identical with published values. (see reference 6)

10. Corossolin (11) was obtained as a waxy solid; $[\alpha]^{25}_D$+82.8° (c 0.34, CHCl$_3$); UV (MeOH) $\lambda_{max}$(log ε) 210 (3.78) nm; UV, MS, ¹H- and ¹³C-NMR were identical with published values. (see reference 7)

11. Corossolone (12) was obtained as a waxy solid; $[\alpha]^{25}_D$+11.7° (c 0.19, CHCl$_3$); UV (MeOH) $\lambda_{max}$(log ε) 206 (3.98) nm; UV, MS, ¹H- and ¹³C-NMR were identical with published values. (see reference 7)

One embodiment of the present invention provides pharmaceutical formulations comprising an effective amount of muricins A-G (1-7) for treating a patient having a tumor. As used herein, an effective amount of the acetogenin compound is defined as the amount of the compound that, upon administration to a patient, inhibits growth of tumor cells, kills malignant cells, reduces the volume or size of the tumors or eliminates the tumor entirely in the treated patient. Thus, the substantially pure compounds in accordance with this invention can be formulated into dosage forms using pharmaceutically acceptable carriers for oral or parenteral administration to patients in need of oncolytic therapy. In one embodiment, a chemotherapeutic composition comprises an anti-tumor effective amount of a compound selected from the group consisting of muricins A-G (1-7) and a pharmaceutically acceptable carrier.

Effective doses will also vary, as recognized by those skilled in the art, dependant on route of administration, excipient usage and the possibility of co-usage with other therapeutic treatments including other anti-tumor agents, and radiation therapy.

The present pharmaceutical formulation may be administered via the parenteral route, including subcutaneously, intraperitoneally, intramuscularly and intravenously. Examples of parenteral dosage forms include aqueous solutions of the active agent, in an isotonic saline, 5% glucose or other well-known pharmaceutically acceptable liquid carrier. In one preferred aspect of the present embodiment, the acetogenin compound is dissolved in a saline solution containing 5% of dimethyl sulfoxide and 10% Cremphor EL (Sigma Chemical Company). Additional solubilizing agents such as cyclodextrins, which form specific, more soluble complexes with the present acetogenin compounds, or other solubilizing agents well-known to those familiar with the art, can be utilized as pharmaceutical excipients for delivery of the acetogenin compounds. Alternatively, the present compounds can be chemically modified to enhance water solubility.

The present compounds can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active acetogenins and solid carriers, and lubricants well-known to those familiar with the art. Examples of solid carriers include starch, sugar, etc. The compounds of the present invention can also be administered in the form of a hard shell tablet or capsule containing, for example, lactose or mannitol as a binder, and conventional fillers and tableting agents.

The cytotoxicities of muricin A-G (1-7) were tested by the three days bioassay against human cancer cell lines, Hep $G_2$ and 2,2,15 according to known procedures and results are shown in Table 6. Adriamycin was used as a standard.

TABLE 6

Cytotoxicity $IC_{50}$ values of compounds 1~12 against human hepatoma cell lines

| Treatments | Human hepatoma cell lines | |
|---|---|---|
| | Hep $G_2$ $IC_{50}$ (μg/mL) | 2,2,15 $IC_{50}$ (μg/mL) |
| Muricin A (1) | 5.04 | $5.13 \times 10^{-3}$ |
| Muricin B (2) | 1.78 | $4.29 \times 10^{-3}$ |
| Muricin C (3) | $4.99 \times 10^{-1}$ | $3.87 \times 10^{-3}$ |
| Muricin D (4) | $6.60 \times 10^{-4}$ | $4.80 \times 10^{-2}$ |
| Muricin E (5) | NT | NT |
| Muricin F (6) | $4.28 \times 10^{-2}$ | $3.86 \times 10^{-3}$ |
| Muricin G (7) | NT | NT |
| Muricatetrocins A&B (8&9) | $4.95 \times 10^{-2}$ | $4.83 \times 10^{-3}$ |
| Longifolicin (10) | $4.04 \times 10^{-4}$ | $4.90 \times 10^{-3}$ |
| Corossolin (11) | $3.53 \times 10^{-1}$ | $2.34 \times 10^{-1}$ |
| Corossolone (12) | $4.80 \times 10^{-1}$ | $2.84 \times 10^{-1}$ |
| Adriamycin | $2.41 \times 10^{-1}$ | $4.50 \times 10^{-1}$ |

NT = non-test

According to Dr. Miyoshi's strategy, the structure-activity relationships of annonaceous acetogenins (1-12) were discussed by being dissected into four chemical portions as following: the hydroxylated THF ring moiety, the α,β-unsaturated γ-lactone ring moiety, and the spacer moiety linking the two rings, and the alkyl side chain attached to THF rings which had a diol group and ended with the terminal methyl.

The NMR spectral and MS data of muricin A and muricin B showed that these two annonaceous acetogenins compounds are steric isomers. For determining the absolute stereochemistry of them, their Mosher ester derivatives were prepared (see Table 2). The only difference between 1 and 2 was the stereochemistries at C-4. The very small but clear difference between (S)- and (R)-MTPA esters permitted us to conclude that the confirmations of C-4 and C-19 of muricin B should be (S) and (R), while the configuration of C-4 and C-19 of muricin A were (R) and (R). Muricin A was the first report that the configuration of the hydroxyl group at C-4 in annonaceous acetogenins could be not only R, but also S. In addition, both muricin A and muricin B are also the first examples of annonaceous acetogenins wherein the THF ring initializes at C-15. Two compounds gave some space to elucidate how the orientations of the terminal lactone ring and a hydroxyl group at C-4 alter their bioactivities (see Table 6). Moreover, these two compounds were the first examples wherein the THF ring began at C-15. Although no annonaceous acetogenins with such a special position of THF ring have been reported in reviews and related papers, it should be reasonable in biosynthesis to form a THF ring in an odd position due to a close polyhydroxyl system.

Interestingly, muricin C is also the first example of annonaceous acetogenins wherein the THF ring began with an odd position, C-17. Muricin D and muricin E, rechecked by HRFAB-MS twice, were reported at the first time that annonaceous acetogenins possessed a C33 skeleton, while most annonaceous acetogenins were thought to possess a C37 or C35 skeleton before.

In this invention, the relationships between bioactivity and stereochemistry of annonaceous acetogenins compounds were concluded as follows:

The role of the stereochemistry of the hydroxyl group at C-4:

Muricin A and muricin B, in which the only difference is the orientations of the hydroxyl group at C-4, revealed to the resembling bioactivities. However, it was clear that muricin A with (R)-hydroxyl group at C-4 was 2.5 times more potent than muricin B with (S)-form to against Hep $G_2$. Although it was indicated in Miyoshi's paper that the presence of the 4-OH group in the spacer region is not essential for the activity, the stereochemical difference of the 4-OH should be the only reason why their bioactivities alter.

The role of the spacer moiety linking the two rings:

In comparison with the cytotoxic value ($IC_{50}$) of muricin C and muricin D, the result revealed that, against 2,2,15, the shorter the length of the spacer moiety, the weaker the potency becomes, but, against Hep $G_2$, the potency was not. Comparison with muricatetrocin A and muricatetrocin B suggested that the appropriate length, approximately 12 carbons (from C-3 to C-14), should be more essential against Hep $G_2$.

The role of hydroxyl groups in the alkyl side chain:

Against Hep $G_2$, comparisons with muricin A, muricin B, and muricin D indicated that the longer the length between the THF ring and the diol group, the weaker the potency becomes.

The role of the double bond in the alkyl side chain:

For annonaceous acetogenins with the mono-THF ring with one flanking hydroxyl group, muricin F showed more cytotoxic than muricin C against either Hep $G_2$ or 2,2,15, which means that the presence of the double bond could raise the bio activity.

Various modifications and variations of the present invention will be recognized by those persons skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

REFERENCE AND NOTES

1. Zeng, L.; Ye Q.; Oberlies, N. H.; Shi, G,; Gu, Z. M.; He, K.; McLaughlin J. L. *Nat Prod. Rep.* 13,275-306, 1996.
2. Zafra-polo, M. C.; Figadere, B.; Gallardo, T.; Tormo, J. R.; Corted, D. *Phytochemistry* 48,1089-1117, 1998,.
3. Alali, F. Q.; Liu, X. X.; McLaughlin, J. L. *J. Nat Prod.* 62,504-540, 1999.
4. Li, C. M.; Mu, Q.; Hao, X. J; Sun, H. D.; Zheng, H. L.; Wu Y. C. *Chin Chem. Lett.* 5,747-750, 1994.
5. Reiser, M. J.; Fang, X. P.; Anderson, J. E.; Miesbauer, L. R.; Smith, D. L.; McLaughlin, J. L. *Helv. Chim. Acta,* 76,2433-2443, 1993.
6. Ye, Q.; alfonso, D.; Evert, D.; McLaughlin, J. L. *Bioorg. Med. Chem.* 4,537-545, 1996.
7. Cortes, D.; Myint, S. H.; Laurens, A.; Hocquemiller, R.; Leboeuf, M.; Cave, A. *Can J. Chem.* 69,8-11, 1991.
8. Riser, M. J.; Hui, Y. H.; Rupprecht, J. K.; Kozlowski, J. F.; Wood, K. V.; McLaughlin, J. L.; Hanson, P. R.; Zhuang, Z.; Hoye, T. R. *J. Am. Chem. Soc.* 114,10203-10213, 1992.

9. Liaw, C. C.; Chang, F. R.; Chen, Y. T.; Chiu, H. F.; Wu, M. J.; Wu, Y. C.; *J. Nat. Prod.* 63,1613-1617, 1999.
10. Chang, F. R.; Chen, J. L. Lin, C. Y; Chiu, H. F.; Wu, M. J.; Wu, Y. C.; *Phytochemistry* 51,883-889, 1999.
11. Chang, F. R.; Chen, Y. C.; Chiu, H. F.; Wu, M. J.; Wu, Y. C.; *Phytochemistry* 51,429-33, 1999.
12. Hoye, T. R.; Hanson, P. R.; Hasenwinkel, L. E.; Ramirez, E. A.; Zhuang, Z. tetrahedron lett. 35,8529-8532, 1994.
13. Cháavez, D.; Mata, R. *J. Nat. Prod.* 61,580,584, 1998.
14. Gawronski, J.; Wu, Y. C.; Polish J. Chem. 73,241-243, 1999.
15. Fujimoto, Y.; Murasaki, C.; Shimada, H.; Nishioka, S.; Kakinuma, K.; Singh, S.; Gupta, Y. K.; Sahai, M. *Chem. Pharm.* Bull. 42,1175-1184, 1994.
16. Doong, S.; L.; Ysai, C. H.; Schinazi, R. F.; Liotta, D. C.; Cheng, Y. C. *Proc. Natl. Acad. Sci.*, USA 88,8495-8499, 1991.
17. Elliott, W. M.; Auersperg, N. Biotech. Histochem. 68,29-35, 1993.
18. Miyoshi, H.; Ohshima, M.; Shimada, H.; Akagi T., Iwamura, H.; Maclaughlin, J. L. *Biochim. Biophysica. Acta*, 1365,443,452. 1998.

What is claimed is:
1. An isolated and purified Annonaceous acetogenin compound having the structure of:
   a. muricin A having the formula of:

said muricin A having an α, β-unsaturated γ-lactone with a hydroxyl group at C-4, a mono-THF ring placed between C-15 and C-18 with one flanking hydroxyl in a threo conformation, two methylene groups of the mono-THF ring corresponding to a trans conformation, two hydroxyl groups at C-26 and C-27 as vicinal diol assigned as threo based, and the stereochemistry at C-34 on the γ-lactone fragment performed in (S)-configuration;
   b. muricin B having the formula of:

said muricin B having an α, β-unsaturated γ-lactone with a hydroxyl group at C-4, a mono-THF ring placed between C-15 and C-18 with one flanking hydroxyl in a trans/threo conformation, two methylene groups of the mono-THF ring corresponding to a trans conformation, two hydroxyl groups at C-26 and C-27 as vicinal diol assigned as threo based, and the stereochemistry at C-34 on the γ-lactone fragment performed in (S)-configuration;
   c. muricin C having the formula of:

said muricin C having an α, β-unsaturated γ-lactone with a hydroxyl group at C-4, a mono-THF ring placed between C-17 and C-20 with one flanking hydroxyl in a trans/threo or threo/trans conformation, two hydroxyl groups at C-24 and C-25 as vicinal diol assigned as threo based, and the stereochemistry at C-34 on the γ-lactone fragment performed in (S)-configuration;
   d. muricin D having the formula of:

said muricin D having an α, β-unsaturated γ-lactone with a hydroxyl group at C-4, a mono-THF ring placed between C-15 and C-18 with one flanking hydroxyl in a threo/trans conformation, two hydroxyl groups at C-22 and C-23 as vicinal diol assigned as threo based;
   e. muricin B having the formula of:

said muricin E having an α, β-unsaturated γ-lactone with a hydroxyl group at C-4, a mono-THF ring placed between C-12 and C-15 with one flanking hydroxyl in a threo/trans conformation, two hydroxyl groups at C-22 and C-23 as vicinal diol assigned as threo based;

f. muricin F having the formula of:

said muricin F having an α, β-unsaturated γ-lactone with a hydroxyl group at C-4, a mono-THF ring placed between C-17 and C-20 with one flanking hydroxyl in a threo/trans conformation, two hydroxyl groups at C-27 and C-28 as vicinal diol assigned as threo based, and a double bond determined at C-24/C-25; or g. muricin G having the formula of:

said muricin G having an α, β-unsaturated γ-lactone with a hydroxyl group at C-4, a mono-THF ring placed between C-16 and C-19 with one flanking hydroxyl in a threo/trans/threo conformation, one hydroxyl groups formed at C-10, a double bond determined at C-23/C-24, and the stereochemistry at C-34 on the γ-lactone fragment performed in (S)-configuration.

2. A method for isolating Annonaceous acetogenins compounds from *Annona muricata* seeds comprising:
extracting said Annonaceous acetogenins compounds from said *Annona muricata* seeds with MeOH to obtain a MeOH extract at room temperature; and
evaporating said MeOH from said MeOH extract; and
partitioning said evaporated MeOH extract in a CHCl$_3$ and aqueous mixture, whereby said Annonaceous acetogenins compounds are in said CHCl$_3$ layer of said CHCl$_3$ and aqueous mixture;
wherein said Annonaceous acetogenins compounds comprise
a. muricin A having the formula of:

said muricin A having an α, β-unsaturated γ-lactone with a hydroxyl group at C-4, a mono-THF ring placed between C-15 and C-18 with one flanking hydroxyl in a threo conformation, two methylene groups of the mono-THF ring corresponding to a trans conformation, two hydroxyl groups at C-26 and C-27 as vicinal diol assigned as threo based, and the stereochemistry at C-34 on the γ-lactone fragment performed in (S)-configuration;

b. muricin B having the formula of:

said muricin B having an α, β-unsaturated γ-lactone with a hydroxyl group at C-4, a mono-THF ring placed between C-15 and C-18 with one flanking hydroxyl in a trans/threo conformation, two methylene groups of the mono-THF ring corresponding to a trans conformation, two hydroxyl groups at C-26 and C-27 as vicinal diol assigned as threo based, and the stereochemistry at C-34 on the γ-lactone fragment performed in (S)-conflguration;

c. muricin C having the formula of:

said muricin C having an α, β-unsaturated γ-lactone with a hydroxyl group at C-4, a mono-THF ring placed between C-17 and C-20 with one flanking hydroxyl in a trans/threo or threo/trans conformation, two hydroxyl groups at C-24 and C-25 as vicinal diol assigned as threo based, and the stereochemistry at C-34 on the γ-lactone fragment performed in (S)-configuration;

d. muricin D having the formula of:

said muricin D having an α, β-unsaturated γ-lactone with a hydroxyl group at C-4, a mono-THF ring placed between C-15 and C-18 with one flanking hydroxyl in a threo/trans conformation, two hydroxyl groups at C-22 and C-23 as vicinal diol assigned as threo based;

e. muricin B having the formula of:

said muricin B having an α, β-unsaturated γ-lactone with a hydroxyl group at C-4, a mono-THF ring placed between C-12 and C-15 with one flanking hydroxyl in a threo/trans conformation, two hydroxyl groups at C-22 and C-23 as vicinal diol assigned as threo based;

f. muricin F having the formula of:

said muricin F having an α, β-unsaturated γ-lactone with a hydroxyl group at C-4, a mono-THF ring placed between C-17 and C-20 with one flanking hydroxyl in a threo/trans conformation, two hydroxyl groups at C-27 and C-28 as vicinal diol assigned as threo based, and a double bond determined at C-24/C-25; and g. muricin G having the formula of:

said muricin G having an α, β-unsaturated γ-lactone with a hydroxyl group at C-4, a mono-THF ring placed between C-16 and C-19 with one flanking hydroxyl in a threo/trans/threo conformation, one hydroxyl groups formed at C-10, a double bond determined at C-23/C-24, and the stereochemistry at C-34 on the γ-lactone fragment performed in (S)-configuration.

3. A pharmaceutical composition comprising said Annonaceous acetogenin compound of claim 1, and a pharmaceutically acceptable carrier.

4. The Annonaceous acetogenins compound according to claim 1, wherein said compound is isolated from *Annona muricata*.

5. The Annonaceous acetogenins compound according to claim 4, wherein said compound is isolated from seeds of *Annona muricata*.

6. A method for separating said Annonaceous acetogenins compounds according to claim 2, comprising:
   collecting said CHCl$_3$ layer;
   loading said CHCl$_3$ layer onto a Si gel column and eluting said Annonaceous acetogenins compounds from said Si gel column with a gradient containing n-hexane-CHCl$_3$ and CHCl$_3$-MeOH into 10 fractions; and
   collecting fraction 7 and fraction 8 eluted from said Si gel column;
   whereby muricin A, muricin B, muricin C, and muricin F are in fraction 7 of the Si gel column; and muricin D, muricin E, and muricin G are in fraction 8 of the Si gel column.

7. The method according to claim 6, wherein said reversed-phased HPLC is an ODS-5 column with MeOH-water at a volume ratio of about 86:14.

8. The method according to claim 6, wherein said muricin A, said muricin B, said muricin C, and said muricin F of said fraction 7 are further separated by a reversed-phase high performance liquid chromatography.

9. The method according to claim 8, wherein said reversed-phased HPLC is an ODS-5 column with MeOH-water at a volume ratio of about 88:12.

10. The method according to claim 6, wherein said muricin D, said muricin E, and said muricin G of said fraction 8 are further separated by a reversed-phase high performance liquid chromatography.

* * * * *